United States Patent [19]

Koss et al.

[11] Patent Number: 4,643,169
[45] Date of Patent: Feb. 17, 1987

[54] DEVICE FOR SELECTIVELY OPENING AND CLOSING TUBULAR ORGANS OF THE BODY

[75] Inventors: Walter Koss, Industriestrasse, 6222 Geisenheim; Udo Jonas, Warmond, both of Fed. Rep. of Germany

[73] Assignee: Walter Koss, Geisenheim, Fed. Rep. of Germany

[21] Appl. No.: 665,107

[22] Filed: Oct. 26, 1984

[30] Foreign Application Priority Data

Nov. 2, 1983 [DE] Fed. Rep. of Germany ... 8331338[U]

[51] Int. Cl.$^4$ .............................................. A61B 19/00
[52] U.S. Cl. ............................ 128/1 R; 128/DIG. 25; 251/4
[58] Field of Search ............... 128/1 R, DIG. 25, 346; 6/326, 327; 251/4, 342

[56] References Cited

U.S. PATENT DOCUMENTS

| | | | |
|---|---|---|---|
| 2,755,060 | 7/1956 | Twyman | 251/342 |
| 3,419,008 | 12/1968 | Plishner | 128/DIG. 25 |
| 3,817,237 | 6/1974 | Bolduc | 128/DIG. 25 |
| 3,882,845 | 5/1975 | Bucalo | 128/1 R |
| 3,924,631 | 12/1975 | Mancusi | 128/DIG. 25 |
| 3,926,175 | 12/1975 | Allen et al. | 128/346 X |
| 3,965,925 | 6/1976 | Gooch | 251/4 |
| 4,408,597 | 10/1983 | Tenney | 128/DIG. 25 |
| 4,523,590 | 6/1985 | Roth et al. | 128/325 |
| 4,552,128 | 11/1985 | Haber | 128/1 R |

FOREIGN PATENT DOCUMENTS

| | | | |
|---|---|---|---|
| 269907 | 2/1914 | Fed. Rep. of Germany | 251/4 |
| 917803 | 2/1963 | United Kingdom | 251/4 |

Primary Examiner—Dalton L. Truluck
Attorney, Agent, or Firm—Gifford, Groh, VanOphem, Sheridan, Sprinkle and Dolgorukov

[57] ABSTRACT

Described is an implantable device for selectively opening and closing tubular organs of the body such as the urethra. The device comprises a sleeve of an elastomeric plastic material, being of a stiff or rigid shape. The sleeve has a slit-like opening for receiving the organ, while the width of the opening is such that the organ is at least partially closed off in the rest condition of the device. Pressure can be applied manually, possibly by way of a remote operating means, to cause the opening to be temporarily enlarged whereby the organ which extends through the opening is also opened. The device may also have a continuously open position which is produced by means of a ball which can be displaced into a retaining seat to hold the opening of the device in an open position.

41 Claims, 23 Drawing Figures

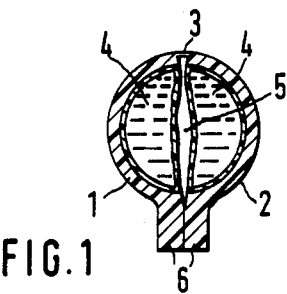
FIG.1
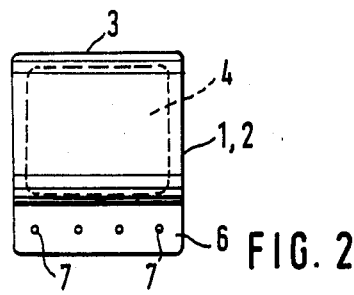
FIG.2
FIG.3
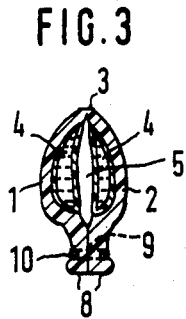
FIG.4
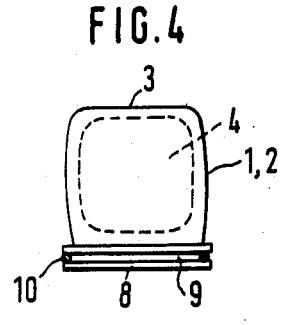
FIG.5
FIG.6 FIG.7
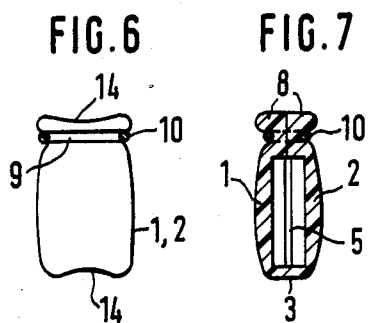
FIG.8
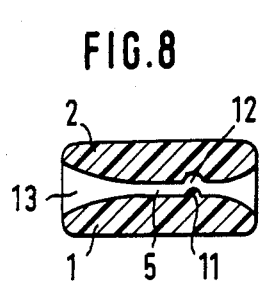

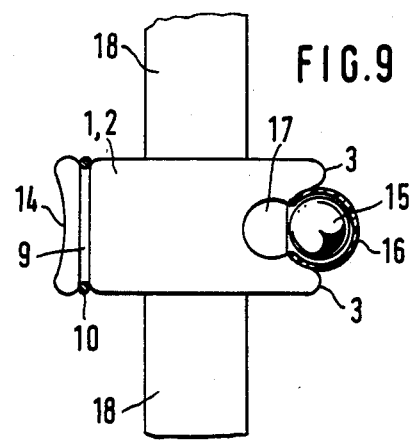
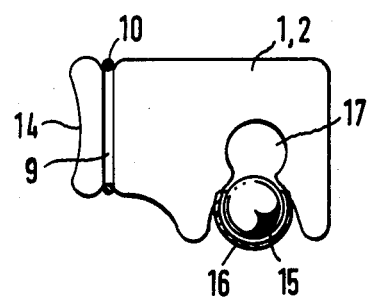
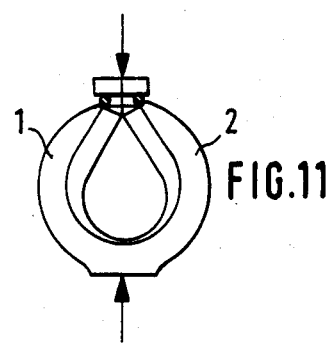
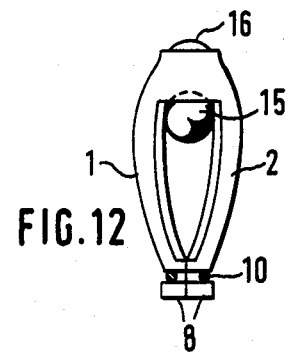
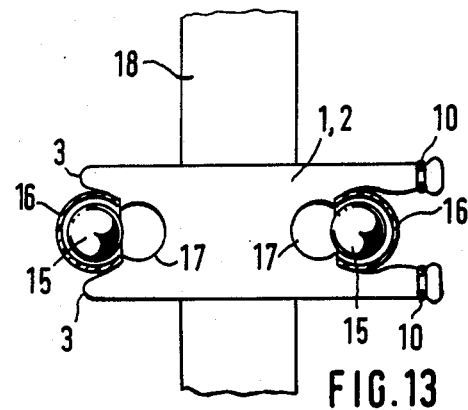

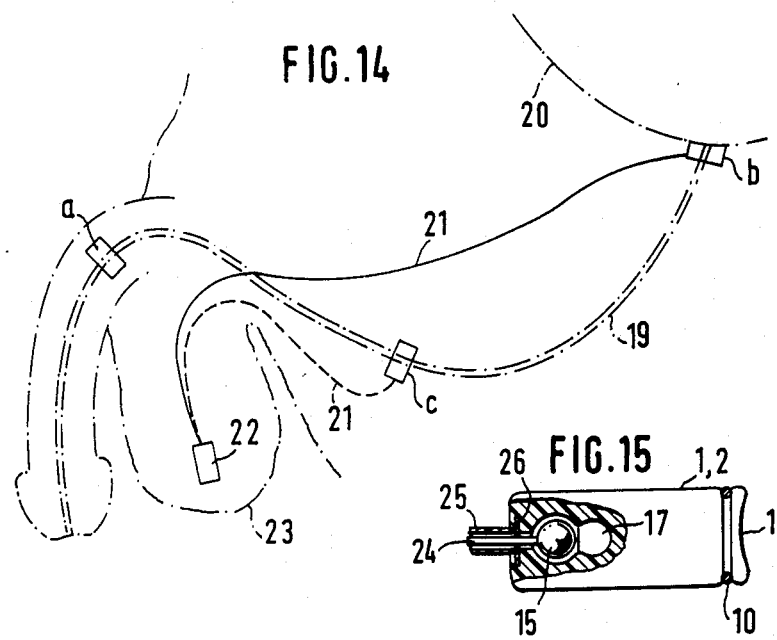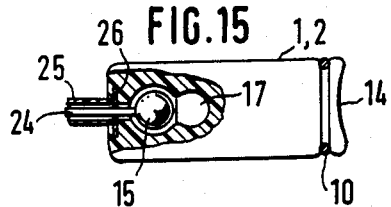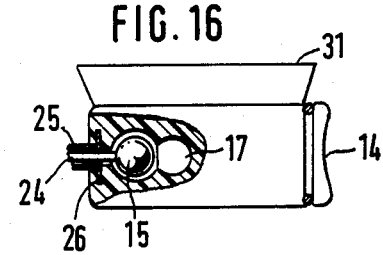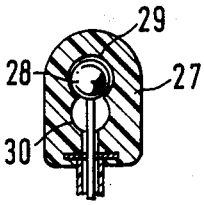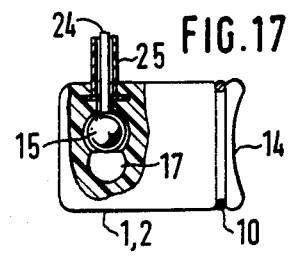

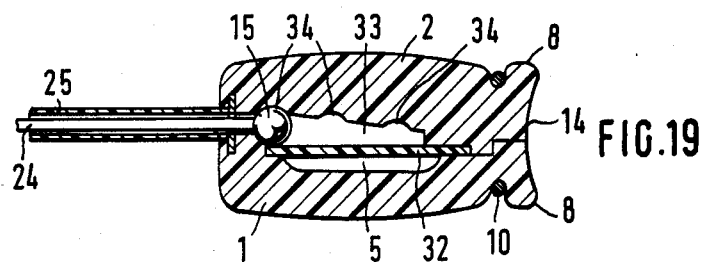
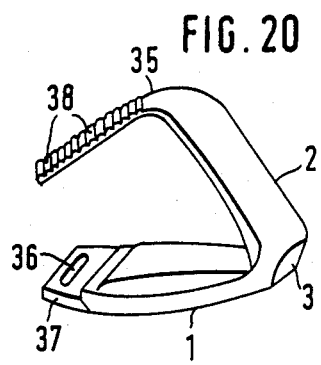
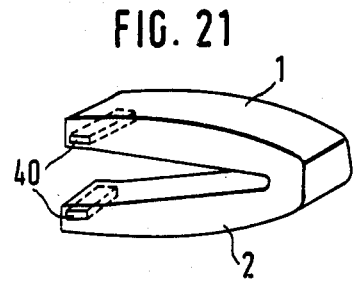
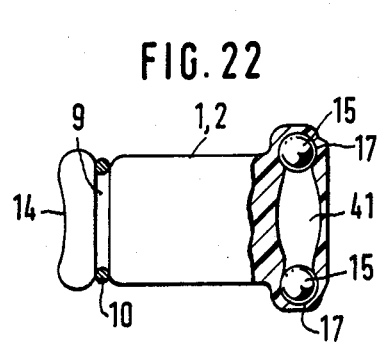
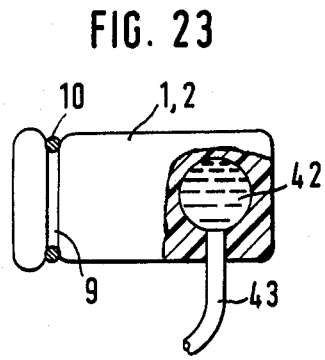

DEVICE FOR SELECTIVELY OPENING AND CLOSING TUBULAR ORGANS OF THE BODY

BACKGROUND OF THE INVENTION

The invention relates generally to a device and in particular to an implantable device for selectively opening and at least partially closing tubular organs of the body, for example the urethra.

Devices for that purpose, which may comprise for example a sleeve of elastomeric plastic material which fits around the organ, are known in the form of prostheses for dealing with urinary incontinence. Such devices are closure arrangements which act on the urethra and which, when the natural sphincter muscle fails, take over performing the function thereof. One such device is for example an implantable urinary incontinence prothesis which is produced in a cushion-like form for silicone rubber and silicone gel and which presses in sponge-like fashion against the urethra in such a way that the urethra is closed as long as a more substantial internal pressure does not occur. Therefore, that arrangement only provides for increasing the resistance to a discharge flow through the urethra, so that the bladder must overcome the respective resistance produced by the device, in order to be emptied. The flow passage cannot be opened and closed as desired.

Another known device is an implantable prosthesis wherein a sleeve which can be pumped up by means of a fluid is positioned around the urethra at the outlet from the bladder. Also implanted are two small pumps which can be operated through the skin, and a fluid reservoir. The sleeve can be filled with one pump, and thus put into the closure condition, while the other pump provides for emptying the sleeve, with the pressure fluid being conveyed into the reservoir. Both the expenditure in respect of the prosthesis itself and also the expenditure in regard to the implantation operation are high. The various components with their comparatively complicated constituent elements increase the danger of failure, which means that repairs become necessary, involving surgical intervention.

Finally, a form of prosthesis for male urinary incontinence is known (German Utility Model No. 79 28 052) wherein a sleeve which fits around the urethra makes it possible to close off the urethra by applying a pressure thereto. The sleeve, at least in a portion thereof, is of such a configuration that that portion can be put into a closure or an open position by a bending effect, with a low degree of spring-back resiliency. The sleeve preferably comprises implantable plastic material with a insert of a material, for example silver, which is easy to bend and which does not have spring-back resiliency. Although such prostheses have proved a success, they are frequently inadequate in particular in regard to the duration of the closure pressure.

Many different problems occur in devices of the kind set forth above, which are also known by the general term of a 'sphincter'. More particularly, the device must be capable of performing the respectively required closing and opening function in a satisfactory manner, and easily and conveniently, without unacceptable pressures or other loadings on the respective organ and the area therearound occurring. Having regard to the fact that the device is to be implanted in the body, the amount of space that it requires must be small. Finally, it should be possible for the implantation operation to be carried out with the utmost simplicity, while the manufacturing cost should not be too high.

SUMMARY OF THE INVENTION

An object of the invention is to provide a device for selectively opening and at least partially closing a tubular organ in the body, which substantially avoids problems which arise in connection with the prior-art devices.

Another object of the present invention is to provide a device for selectively opening and at least partially closing a tubular organ in the body, which is convenient and comfortable to operate while satisfactorily performing the closure function.

A further object of the invention is to provide a device which can be implanted in the body, for selectively opening and closing a tubular organ, which is simple to produce and to implant.

Those and other objects are achieved by a device, more particularly an implantable device, adapted selectively to open and at least partially close a tubular organ in the body such as the urethra, comprising a sleeve of elastomeric plastic material which embraces the organ. The sleeve is of an inherently rigid configuration, thereby forming a relatively stiff member, and has a slit-like or crack-like through opening for the organ. The width of the slit or crack is such that the organ is at least partially closed off.

Although a preferred embodiment of the device constitutes a urinary incontinence prosthesis, the device in accordance with the principles of this invention can also be used on virtually any other tubular organ, for example on the ureter for preventing a back flow of urine from the bladder towards the kidney. When portions of the small or large intestine are cut out, the respective portion of the intestine may become the reservoir which is rendered continent by means of such a sphincter arrangement. In that connection, the discharge may be to the skin or also in the form of a connection to other organs in the body, for example the bladder, the vagina, cavities which are formed by surgical operations or to other portions of the intestine. The device can also be put to use in the region of the oesophagus or in conjunction with portions of the stomach, to act as a closure mechanism both in regard to natural organs of the body and also in regard to foreign bladder replacement organs. In addition, the sphincter device according to the present invention may be used to provide for stool continence and finally also for constricting or for closing off certain areas of blood vessels in order temporarily to interrupt or reduce the flow of blood.

The various situations in which the device can be used require it to be adapted thereto in regard to dimensions, external shape, width of the slit or crack and the respective return force required. Those skilled in the art can generally deal with such aspects. Special circumstances in that respect will be described hereinafter.

The pressure which is applied to the organ disposed in the slit or opening in the device and which causes the closure or partial closure function may be controlled by means of the size of the width of the slit or crack as well as the inherent stiffness of the sleeve and the configuration of the opening. The term 'inherent stiffness' is used herein to denote the force which is required for altering the shape of the sleeve, or also the elastic return force which occurs after deformation of the sleeve.

Although the term slit-like through opening or slit is used herein in particular to denote a straight slit, it also denotes a slit which is curved or which has a plurality of bends, or an annular slit or opening. In the broad sense therefore the term slit is intended to denote any through opening, the lumen of which can be influenced by external forces.

The device according to the invention may be of such a design that in the rest condition it at least partially closes off the organ which is passes through the opening, an increase in the width of the opening of the sleeve being required in order to open the organ, the width of the opening of the sleeve being increased more particularly by deformation of the sleeve. However, the arrangement may also be such that the open position is the rest position of the device and the width of the slit or opening is reduced for at least partially closing off the organ on which the device is used.

Further aspects and embodiments of the invention are set forth in the claims hereinafter. Thus, the sleeve may comprise two half shell portions which are connected together by way of a hinge means and the free ends of which can be joined together after the device has been fitted to the organ. Desirably, the hinge means is formed by a thin portion of the sleeve, being for example in the form of a film hinge. Although in some cases it is possible for a closed sleeve to be pushed over the respective organ which is to be closed off thereby, in many cases such as for example in the case of the urethra, the organ would first have to be severed in order for the sleeve to be fitted thereon, and that can result in complications. Therefore, in most cases, a sleeve of an open construction, which can be fitted around the organ by means of the hinge arrangement, is more desirable. After the sleeve has been fitted in place, the two free ends of the half shell portions of the sleeve can be sewn together, for which purpose the free ends of the two half shell portions are desirably formed by flaps or tabs. However, in accordance with a further feature of the invention, the two half shell portions of the device may be joined together by means of a connecting clamp or a resilient ring, if the free ends, on the outside thereof, each have a receiving groove for accommodating the clamp or the ring. Another possible construction provides that a magnetic closure is disposed at the free ends of the sleeve of the device. For that purpose, a permanent magnet in the form of a bar or a ring may be fitted into each free end of the sleeve, the polarities of the magnets being such that the magnets attract each other. One permanent magnet may also be replaced by a ferromagnetic material. The maximum holding force, besides being governed by the magnetic properties, is also defined by the air gap which remains in the closed condition. If the two magnets are in direct contact with each other, the holding force which holds the sleeve in a closed position is at its highest. In that case however it is necessary to use a magnetic material which is suitable for implantation. If the permanent magnets are embedded in the sleeve, then there remains at least a thin skin between the magnets, thereby holding them spaced apart, and the holding force produced by the co-operation of the magnets may be adjusted by varying the thickness of the material between the two magnets. In addition to the permanent magnets, it is possible to provide a guide means which prevents lateral displacement of the two free ends of the sleeve, in particular when the device is in the open condition. To provide the guide action, for example a pin may be provided at one free end on one of the half shell portions of the sleeve, the pin engaging a corresponding bore in the end of the other half shell portion. Finally, it may be provided that the two free ends of the half shell portions, including the magnets, are enclosed or encased by a bag or pouch of thin plastic material. The bag or pouch prevents body tissue from growing or passing into the gap between the closure portions. As the bag can only be fitted after the organ of the body has been inserted into the sleeve of the device, the bag must also having corresponding slots.

Instead of the magnetic closure arrangement, the device may also have a press-button closure disposed at the free ends of the portions of the casing, and that closure can also be enclosed by a bag or pouch.

Another form of connection which additionally permits the width of the opening in the sleeve to be adjusted provides that the one free end of the sleeve has a strip-like or band-like extension portion with retaining beads or projections, while the other free end has a through opening which is matched to the form of the above-mentioned extension portion. The extension portion is then fitted through the opening and tightened until the required width of slit or opening in the sleeve is achieved, with the sleeve being progressively tightened by successive engagement with each of the beads or projections on the extension portion.

The sleeve itself may be of many different configurations. Thus, a further aspect of the invention provides that the sleeve is of circular or oval cross-section and on its inside has gel-filled cushions which define the slit-like opening between them. The gel-filled cushions make it readily possible to provide for uniform distribution of pressure, with a cushioning effect. In another form of the invention, the sleeve may be of substantially square or rectangular cross-section having two mutually oppositely disposed walls which between them define the opening through which the organ of the body passes. As this form of the device does not use additional gel cushions, it does not suffer from the danger, which is a difficulty in many situations of use, that the sleeve and the cushions age in different ways, which could give rise to changes in the shape of the device. Actuation of the closure means formed by the device can be simplified by the narrow sides of the sleeve, being the sides which extend parallel to the opening through which the organ is passed, having gripping depressions.

In order to adapt the device to the shape of the organ which is passed through the opening therein or to the shape that the organ adopts by virtue of bulging after the device is closed therearound, another aspect of the invention may advantageously provide that the through opening for accommodating the organ is enlarged at the entry end in a funnel-like shape, in the direction of flow through the organ. The shut-off action of the device may be improved, without exerting an excessively high pressure, if, in accordance with a further aspect of the invention, a boundary wall of the opening through which the organ extends has at least one bead portion or the like which extends transversely with respect to said opening. In addition, a channel or groove which is in opposite relationship to the above-mentioned bead means may be formed in the other boundary wall of the opening for receiving the organ.

For the purposes of fixing the closure device at the respective point of implantation thereof, the invention may provide in an advantageous feature thereof that plastic threads or a fabric or felt strip or portion of plastic threads are arranged on the sleeve. That construction may be provided by embedding same on at least one side of the opening through which the organ extends and/or at the narrow sides of the sleeve. Eyes or loops may also be formed from the threads.

It is frequently necessary or at any event advantageous for a closure device according to the invention to have not only a continuously closed position which can be temporarily altered by applying a pressure to put the device into the open position, in such a way that for example urine can be discharged, but also to have the possibility of providing a continuously open position. A continuously open position may be used for example after the operative implantation process, in order to permit a free discharge of urine until the healing process has taken place. In addition, the device may be set in the continuously open position in order to protect the vessel which is closed by the device, for example overnight, because in that situation the problem of incontinence can be dealt with in a different manner. In order to provide for such a possibility, an embodiment of the invention provides that an outwardly closed chamber having at least one enclosed member which can be displaced from the outside is provided at least at one narrow side of the slit-like opening in the sleeve. The above-mentioned displaceable member is preferably a ball. In that form of the device, the space in which the displaceable member or ball is carried may desirably be provided with a seat, disposed in a direction towards the opening through which the organ extends, the seat being adapted to accommodate and retain the ball in such a way as to hold the device in a continuously open position. More specifically, moving the above-mentioned body such as a ball causes the slitlike opening to be enlarged, which means that the device is in an open position. The construction may be such that applying a slight pressure to the sleeve causes the device to be temporarily opened, and it is only when a stronger pressure is applied to the sleeve that the above-mentioned member or ball is displaced in such a manner, possibly engaging into the above-mentioned seat, that the device remains permanently in the open position. The device can be subsequently returned to the continuously closed position by applying manual pressure to the device in order to return the above-mentioned member or ball to its inoperative position. The space which accommodates the displaceable member or ball and also the position of that space may vary. Thus, the space may be disposed substantially in the plane of the slit-like opening through which the organ extends, and transversely with respect to the direction of flow in the tubular organ or parallel to the direction of flow. The space which extends parallel to the direction of flow through the organ may have a respective seat for a respective ball, at each of its two ends. When the two balls are disposed in their respective seats, then the organ of the body is closed off. If a pressure is applied to the two balls, preferably using two fingers of a hand, so that the balls are moved out of their seats into the interposed part of the space in which the balls are movable, then the sleeve is opened. In order to facilitate moving the displaceable member or ball, a further aspect of this embodiment provides that a lubricant is introduced into the space which accommodates the displaceable member or ball. The lubricant may be for example a gel or a powder.

Depending on the situation of use of the closure device, the device may also be implanted in such a way that it can be operated from the exterior, through the skin. However, there are also situations where the closure device cannot be easily felt and operated, for example when it is used on a urethra at the exit from the bladder. For that purpose, another embodiment of the invention provides that the displaceable member such as a ball is provided with a remote actuating means in the manner of a remote operating device for a photographic camera. In that case, when the closure device is fitted at the exit from the bladder, in the situation referred to above, the actuating member of the remote operating device may be disposed for example in the scrotum or the labia majora of the vulva. The remote operating device desirably comprises a stiff plastic tube which is embedded in silicone rubber, and an actuating member which is slidably mounted in the plastic tube and which can be displaced from the outside and which acts on the displaceable member or ball. The actuating member may be a metal wire, a cable, a monofilic plastic wire or a coil member which is rigid with respect to pressure applied thereto.

Another embodiment of a device according to the present invention provides that provided at least in a wall of the opening through which the organ passes is a space which is closed off with respect to that opening by a thin skin portion, while a member such as a pin or a ball is displaceable in that space, thereby altering the width of the opening through which the organ passes. When that member such as the pin or ball is displaced, by virtue of a suitable configuration with respect to the space which is closed off by the thin skin portion, being in particular of a wedge-like shape, the arrangement provides that as the member is displaced, the skin portion is curved out to a greater or lesser degree, thereby altering the width of the slit-like opening, and closing off or constricting or opening the organ which extends therethrough. The above-mentioned term thin skin portion denotes a structure which is less rigid in respect of shape than the associated wall of the sleeve so that, when the member or ball or pin is displaced, it is the skin portion which is deformed and not the sleeve. In contrast to the embodiments described hereinbefore, this construction gives a continuously open position, and the device is moved into a constriction position or a closure position only by the member or ball or pin being displaced. The space in a wall of the through opening of the sleeve may advantageously have one or more retaining or detent means for the displaceable member, so that the device can be easily and comfortably set into the respective positions defined thereby. The above-described remote operating arrangement may also be used, with advantage, in this embodiment.

In order to provide the open or closed position or a continuously set position, a further embodiment of the invention provides that, instead of the above-mentioned closed space with a member displaceable therein from the exterior, a closed pressure space or chamber is provided at at least one narrow side of the slit-like opening through which the organ extends, the pressure chamber communicating with a pump means, wherein the chamber and the pump means are filled with a pressure fluid. The pump means may be arranged close to the sleeve and may be for example formed integrally therewith, but it is also possible to provide for remote operation, by connecting the sleeve and the pump by way of a tube or hose. In the simplest case, the pump means may comprise a pressure pad or cushion, but it is also possible to use a piston-type pump having a displaceable piston. The device can be set in the continuously open or continuously closed position for example by the provision of a valve to prevent a back flow, in the communication between the pressure chamber and the pump means.

In all the embodiments described herein, polytetrafluoroethylene (Teflon) may be used as the material for the displaceable member such as a ball. A ball or member of that material is light and smooth and is also not adversely affected by the diffusion of fluids therein after the implantation operation. The sleeve is desirably made from silicone rubber of an acceptable quality for medical purposes. In that connection, different grades of hardness may be used for the various components of the devices. However, it is also possible to use other materials, for example balls of stainless steel or sleeves of other plastic materials, for example polyurethane.

Further objects, features and advantages of the present invention will be apparent from the following description of embodiments which are given by way of example of the teachings of this invention.

BRIEF DESCRIPTION OF THE DRAWINGS

FIGS. 1 and 2 show a cross-sectional view and a side view respectively of an embodiment of the invention, which is of circular cross-section and which has gel cushions therein, FIGS. 3 and 4 show a further embodiment of the invention, which is of oval cross-section with gel cushions therein, FIG. 5 shows a closure clamp or clip for the embodiment shown in FIGS. 3 and 4, FIGS. 6 and 7 show a side view and a cross-sectional view respectively of an embodiment of the invention which is of rectangular cross-section, without using gel cushions, FIG. 8 shows a view in longitudinal section on an enlarged scale through the embodiment illustrated in FIGS. 6 and 7, FIG. 9 shows an embodiment similar to that shown in FIGS. 6 through 8, wherein however the device can be set in a continuously open position, FIG. 10 shows a modification of the embodiment illustrated in FIG. 9, FIGS. 11 and 12 show an embodiment which is similar to that shown in FIG. 9, wherein the closure device is opened by applying a pressure or is put into a continuously open position by means of a ball.

FIG. 13 shows an embodiment which is similar to that shown in FIG. 9, which however uses balls in order to provide for the continuously open position, on both sides of the sleeve, FIG. 14 is a diagrammatic view of the options of fitting the device on a urethra in a man, FIG. 15 shows an embodiment which is similar to that illustrated in FIG. 9, with additional remote operation, FIG. 16 shows a modification of the embodiment illustrated in FIG. 15, FIG. 17 shows a further modification of the embodiment illustrated in FIG. 15, FIG. 18 shows the actuating member of a remote operating arrangement for the embodiment illustrated in FIGS. 15 through 18, FIG. 19 shows a further embodiment of the invention, FIG. 20 shows a modification of the embodiment illustrated in FIGS. 6 through 8, with an opening of adjustable width, FIG. 21 shows an embodiment of the invention having a magnetic closure arrangement, FIG. 22 shows a modification of the embodiment shown in FIG. 10, having two displaceable balls, and FIG. 23 shows an embodiment of the invention which has hydraulic actuation.

DESCRIPTION OF PREFERRED EMBODIMENTS

Referring firstly to FIGS. 1 and 2, the embodiment illustrated therein by way of example comprises a split sleeve formed by two half shell portions 1 and 2 of silicone rubber, which are connected together by way of a film hinge 3 which is only shown in diagrammatic form. Disposed in the interior of each of the half shell portions 1 and 2 is a respective cushion or pad 4 which is filled with a gel and between which is disposed a slit-like through opening 5 for receiving the respective organ which is to be closed off, for example the urethra in a human being. On the side that is remote from the film hinge 3, the half shell portions 1 and 2 have flaps or tabs which are formed thereon and which permit a permanent joint to be made therebetween for example by sewing, after the sleeve has been fitted for example to the urethra. Preformed bores or holes 7 are provided in the flaps or tabs 6, to facilitate making the connection between the flaps or tabs. The width of the opening 5 is such that, in the rest position illustrated in FIG. 1, a urethra (not shown) which is passed through the opening is closed by applying pressure to the walls of the opening. In that connection, the setting of the device may be such that the urethra is still closed off up to a given pressure applied thereto, for example a pressure of 70 cm water column, so that emergency discharge can be produced, above that pressure. The open position of the device is produced by a lateral pressure being applied by means of the fingers between the film hinge 3 and the flaps or tabs 6. The opening 5 is then widened and permits a free flow through the urethra. If a stronger pressure is applied, then the opening is closed off again because the opening 5 is then constricted in a transverse direction. That may be a desirable consideration in some situations of use.

The embodiment shown in FIGS. 3 and 4 differs from the embodiment shown in FIGS. 1 and 2 by virtue of the oval cross-sectional shape of the half shell portions 1 and 2 and the nature of the means for joining the half shell portions 1 and 2 together. The free ends of the half shell portions 1 and 2, being therefore the ends remote from the film hinge 3, have bead-like enlargements 8 behind each of which is provided an insertion groove 9. A clamp or clip 10 comprising for example stainless steel, as shown in FIG. 5, can be fitted into the groove 10 and secured therein be being bent shut. By virtue of the oval shape of the embodiment shown in FIGS. 4 and 5, the opening 5 can be enlarged to a greater degree, for example for passing a catheter or an endoscope, or also for discharge purposes.

The embodiment shown in FIGS. 6 to 8, unlike the above-described embodiments, does not have any gel cushions or pads 4. In this embodiment, the slit-like opening 5 is disposed directly between the half shell portions 1 and 2. As can be seen from the cross-sectional view on an enlarged scale in FIG. 8, a transverse bead portion or projection 11 is additionally provided in one half shell portion 1, in the opening 5, while disposed opposite thereto is a matchine groove 12 in the other half-shell portion 2. The co-operation of the bead portion 11 and the groove 12 is intended to improve the shut-off or sealing effect. The bead portion 11 and the groove 12 are not in the middle in the opening 5, but are displaced somewhat towards the exit, the direction of flow through the opening being from left to right in the view shown in FIG. 8. At the entry side (with respect to the direction of flow) the opening 5 has a funnel-like enlargement 13 which represents a configuration that is adapted to the shape of a urethra (not shown) which passes through the opening 5, if it is considered that the urethra swells up or bulges after it has been closed off. Once again, the sphincter device shown in FIGS. 6 through 8 is opened by a pressure being applied to the narrow sides thereof, the application of pressure being facilitated by gripping troughs or depressions 14. In addition, the funnel-like configuration 13 can provide a short-term improvement in the shut-off or sealing action of the device. More specifically, if the funnel configuration 13 is expanded somewhat for example when the person using the device coughs, the walls of the half shell portions 1 and 2 come closer together at the exit end, being at the right-hand end in FIG. 8, thereby reducing the width of the opening through which the organ is passed and thus enhancing the closure effect.

In the embodiment illustrated in FIG. 9, in addition to the closed position and the short-term open position which is produced by applying a pressure, the illustrated construction also provides a continuously open position, by virtue of including a displaceable member illustrated in the form of a ball 15 of plastic material, which is disposed in a space or chamber which is sealed and closed off with respect to the exterior by a bag or pouch 16, in the region between the divided film hinge 3. Under a pressure applied from the outside, the ball 15 can be displaced towards the left in FIG. 9 into a seat 17, in which case the slit-like opening 5 is enlarged and the device is put into a continuously open position. That position is shown in FIG. 12. FIG. 11 additionally shows that it is also possible to produce a large opening, without a ball, by simply applying a pressure.

In the embodiment illustrated in FIG. 9, the space in which the ball 15 is accommodated extends, in regard to the direction of movement of the ball 15, substantially in the plane of the slit, that is to say, in the plane of the slit-like opening 5 through which the organ extends, and at the same time transversely with respect to the direction of flow through the organ, being downwardly in the view shown in FIG. 9. The embodiment illustrated in FIG. 10 is modified to the effect that, although the space which accommodates the ball 15 also extends in the plane of the slit-like opening 5, it is parallel to the direction of flow through the organ, being downwardly in the view shown in FIG. 10.

The embodiment illustrated in FIG. 13 corresponds to the embodiment shown in FIG. 9, but in addition, on the side at which the two half shell portions 1 and 2 are connected together after the device has been fitted to the organ on which it is to be used, the FIG. 13 embodiment also has a closed space or chamber accommodating a displaceable member such as a plastic ball 15. In that case, the above-mentioned space or chamber cannot be disposed between the two half shell portions 1 and 2 (see FIG. 12) but must be disposed in one of the half shell portions 1 or 2, to provide a sealing action. By virtue of the two balls 15 being pressed into their seats 17, the device can form a large symmetrical opening, with a continuously open position, unlike the embodiment illustrated in FIG. 9, the FIG. 13 embodiment uses two closure clips or clamps 10.

In all embodiments which provide for a continuously open position, making use of a displaceable member such as a ball, the respective space which accommodates the ball is preferably filled with a lubricant such as a gel or a powder (not shown), in order to improve the slidability of the ball in the space or chamber. The embodiments of FIGS. 9 and 13 also show that a fabric or woven strip 18 of plastic threads may be vulcanised into one of the half shell portions 1 and 2 or into both thereof. The strip 18 simplifies fixing the sphincter device at the respective location at which it is to be implanted.

FIG. 14 diagrammatically shows the locations on the urethra 19 at which a closure device in accordance with one of the embodiments of the invention can be fitted, in a male. If the device is arranged at the location indicated at a in the region of the penis, the device can be directly actuated by applying pressure using the fingers. The embodiments shown in FIGS. 1 through 13 can accordingly be used. If on the other hand the closure device is arranged at the location indicated by b at the exit from the bladder 20 or at the location indicated at c, beneath the floor of the pelvis (not shown), the device cannot then be readily actuated in a direct fashion. In that case, use is made of a remote operating arrangement 21 which is of a similar construction to a remote shutter release for a photographic camera. In that case, the actuating member 22 of the arrangement 21 is disposed for example in the scrotum 23. In a corresponding fashion, the actuating member for a remotely-operable closure device at the exit from the bladder in a female may be disposed in the labia majora of the vulva.

FIG. 15 shows a first embodiment of a bladder sphincter device which has a remote operating arrangement. This construction corresponds to the embodiment shown in FIG. 9, except that the plastic ball 15 is not displaced by directly applying a pressure but is moved by means of a steel wire or a coil member 24 which runs in a tube or hose 25 of strong plastic material. The anchoring 26 of the tube or hose 25 is shown in diagrammatic form in FIG. 15, as a plate 26.

Reference will be made at this point to FIG. 18 showing the associated actuating member 27 to which the tube or hose 25 with the coil member 24 therein extends. The actuating member 27 which is also made for example from silicone rubber contains, in a closed space or chamber, a plastic ball 28 which is secured to the coil member 24 and which is displaceable between two seats 29 and 30. In the position of the arrangement shown in FIGS. 15 and 18, the sphincter device is closed. If the ball 28 and therewith the ball 15 are only slightly displaced by the application of a pressure, but without going from the seat 29 into the seat 30, then the slit-like opening 5 is enlarged to such a degree as to provide for sufficient opening to enable the bladder to be emptied. The device can then be returned to the closed position by releasing the pressure. It is only if the ball 28 is urged into the seat 30 by passing over a detent mean which is formed between the seats 29 and 30 by virtue of the internal configuration of the member 27, that the ball 15 is also moved into its other seat so that the device is then moved into a continuously open position which can also be used, and frequently more conveniently, for the bladder emptying operation. It will be appreciated that the above-described short-term or temporary open position can also be used in the embodiments illustrated in FIGS. 9, 10 and 13.

Referring now to FIG. 16, the embodiment illustrated therein differs from that shown in FIG. 15 only by virtue of the additional provision of a funnel-like projection 31 on the entry end of the opening 5. The portion 31 permits the device to be adapted and matched to the neck of the bladder as indicated at b in FIG. 14. The embodiment of the device shown in FIG. 15 may be fitted for example at location c in FIG. 14.

Referring to FIG. 17, the construction illustrated therein is a modification of the embodiment shown in FIG. 15, similar to the modified embodiment shown in FIG. 10; in this embodiment, the space or chamber for the ball 15 and accordingly the path of movement of the coil member 24 are parallel to the direction of flow through the organ (being vertical in FIG. 17).

FIG. 19 shows an embodiment which is also actuable by a remote operating arrangement, but it also differs on a number of points from the embodiments described hereinbefore. More specifically, in the FIG. 19 construction, the opening 5 is disposed between the wall of one half shell portion 1 and a comparatively thin skin portion 32. The position illustrated in FIG. 19 corresponds to the open position of the device, if it is considered that for example a urethra extends through the opening (being normal to the plane of the drawing), beneath the skin portion 32, and in so doing causes the skin portion 32 possibly to be slightly curved upwardly, by virtue of its natural or inherent elasticity. In order for the urethra or like organ to be partially or completely shut off, the ball 15 must then be displaced by means of the coil member 24 from the illustrated position in a space or chamber 33 which tapers down in a wedge-like configuration; when the ball 15 is displaced in the chamber 33, the skin portion 32 is increasingly pressed towards the organ which is to be shut off. Reference numeral 34 in FIG. 19 denotes retaining or detent means for the ball 15, to permit the device to be set in certain positions of defining a given flow through the organ on which the device is fitted. Unlike the embodiments described hereinbefore therefore, the embodiment shown in FIG. 19 is in a continuously open position when in the rest condition, and can be operated from the continuously open position into the partially or completely closed position. It will be appreciated also that the constructions of the above-described embodiments may also be changed in a comparatively simple manner in such a way that they move into a continuously closed position when the ball or balls are operated or pressed into the associated seat.

The embodiment shown in FIG. 20 represents a modification of the embodiment shown in FIGS. 6 through 8. Instead of the two half shell portions 1 and 2 being joined together and closed off by means of a clamp or clip 10 as shown for example in FIGS. 6 and 7, the FIG. 20 embodiment provides that the one half shell portion 2 has a strip-like extension portion 35 which can be passed through an opening 36 in a flap or tab 37 on the other half shell portion 1. The extension portion 35 is provided with retaining or detent projections in the form of transversely extending bead portions 38 of substantially square or rectangular cross-section, so that the strip portion 35 can be inserted into the opening 36 as far as a desired position, that is to say, to set the device at a given width in respect of its opening 5, and the strip portion 35 can then be fixed in that position in the opening 36 by the detent or retaining action of the bead portions 38. The strip portion 35 may desirably comprise a harder material (silicone rubber) like the half shell portions 1 and 2. A closure arrangement similar to that used in the embodiment illustrated in FIG. 20 may also be employed in the other embodiments described herein.

In a further embodiment of the invention as shown in FIG. 21, the two half shell portions 1 and 2 are spread in the rest position illustrated. When a pressure is applied to the two free ends of the half shell portions 1 and 2, two magnetic bars 40 which are embedded therein move towards each other. The magnetic bars 40 comprise permanent-magnetic material, being of such a magnetisation and polarity that they attract each other. The magnitude of the holding force for holding the free ends of the half shell portions 1 and 2 together may be determined by the strength of the magnets and also the thickness of the portion of plastic material which remains between the magnets when the half shell portions 1 and 2 are pressed together. The surface of the magnets may also project out of the plastic material so that it is possible to produce a very high holding or sticking force in that case, by virtue of the two magnets being directly in contact with each other. In order to ensure that tissue does not grow into the gap between the magnets 40, particularly when the device is in the open condition, the free ends of the half shell portions 1 and 2 may be enclosed by a bag or pouch (not shown).

Referring now to FIG. 22, shown therein is an embodiment which represents a modification of the embodiment illustrated in FIG. 10. In this embodiment also, there is a space or chamber 41 which extends parallel to the direction of flow through the organ to which the device is to be fitted. In this embodiment however, the space 41 contains two members illustrated as balls 15. In the rest position as illustrated, that is to say, when the flow through the organ is shut off, the balls 15 are each disposed in a respective seat 17 at the end of the space 41. In order to put the device into a continuously open position, pressure is applied to both balls 15, preferably using the fingers of one hand, so that the balls 15 then leave their seats 17 and move substantially into the middle of the space 41, spreading the two half shell portions 1 and 2 open. The two balls 15 can be returned to their respective seats 17 by applying finger pressure in the transverse direction.

FIG. 23 shows a further embodiment of the device in accordance with this invention. Unlike the above-described embodiments, the two half shell portions 1 and 2 are not opened and closed by manually applying a pressure and possibly displacing a ball, but instead the device is provided, at one narrow side, with a closed pressure space or chamber 42 which communicates by way of a pipe or hose 43 with a pump means (not shown). The pressure chamber 42, the pipe or hose 43 and the pump means are filled with a pressure fluid so that, when the pump means is actuated, the pressure chamber 42 is enlarged and thus the device can be moved into the open condition. The volume of pressure fluid required for opening the device is only very small and is for example about 1 ml. The pump means may comprise a pressure chamber (not shown) which is disposed on the sleeve formed by the half shell portions 1 and 2. However, such a pressure chamber or another form of pump means may also be disposed at a remote location, being connected by way of a longer pipe or hose 43, so as to permit remote actuation of the device. If it is desired for the device to have a continuously open position, either the pump means must be of a suitable construction or a valve (not shown) which acts in one direction can be disposed in the pipe or hose 43.

Various modifications and alterations may be made in the above-described embodiments of the present invention without thereby departing from the spirit and scope thereof.

What is claimed is:

1. A device such as an implantable device for selectively opening and at least partially closing tubular organs of the body, comprising a sleeve of elastomeric plastic material adapted to embrace the organ, wherein the sleeve has a slit-like through opening for the organ, the width of the opening being such that the organ is at least partially closed off; said slit-like opening defining a plane through said sleeve, and said organ defining a first direction of fluid flow through said organ which lies in said plane; and wherein the elastomeric plastic material of said sleeve is relatively stiff but manually resiliently deformable in a second direction in said plane of said slit-like opening and transverse to said direction of flow through said organ, so that said opening expands upon the manual application of pressure to said sleeve in said second direction.

2. A device as set forth in claim 1 wherein the sleeve comprises first and second half shell portions having first and second ends, a hinge means connecting said half shell portions together at their first ends, and means at said second ends of said half shell portions for connecting them together after the sleeve has been fitted around a said organ.

3. A device as set forth in claim 2 wherein said hinge means comprises a reduced-thickness portion of the sleeve.

4. A device as set forth in claim 3 wherein said reduced-thickness portion is a film hinge.

5. A device as set forth in claim 2 wherein said means at said second ends of said half shell portions comprise tabs which are adapted to be sewn together.

6. A device as set forth in claim 2 wherein said second ends of said half shell portions, on the outside thereof, each have a receiving groove for accommodating a clamping connecting member.

7. A device as set forth in claim 2 wherein a magnetic closure means is disposed at said second ends of said half shell portions.

8. A device as set forth in claim 2 wherein a press fastener closure means is disposed at said second ends of said half shell portions.

9. A device as set forth in claim 2 wherein said second end of one of said half shell portions has a strip-like extension portion having detent means thereon and the second end of the other half shell portion has an aperture adapted to receive said strip-like extension portion.

10. A device as set forth in claim 1 wherein said sleeve is of annular configuration and is provided on the inside thereof with gel-filled pads for defining said opening therebetween.

11. A device as set forth in claim 1 wherein said sleeve is of oval configuration and is provided on the inside thereof with gel-filled pads for defining said opening therebetween.

12. A device as set forth in claim 1 wherein said sleeve is of substantially rectangular cross-section and has two oppositely disposed wall portions defining said opening therebetween.

13. A device as set forth in claim 12 wherein said sleeve has narrow sides extending parallel to said opening, and wherein gripping depressions are provided in said narrow sides.

14. A device as set forth in claim 1 wherein said opening is enlarged in a funnel-like configuration at the entry end of the sleeve as considered in the direction of flow through said organ.

15. A device as set forth in claim 1 wherein a wall portion defining said opening has at least one raised portion thereon, extending transversely with respect to said opening.

16. A device as set forth in claim 15 wherein said sleeve has a further wall portion in oppositely disposed relationship to said first-mentioned wall portion, and wherein a recess is provided in said further wall portion, in opposite relationship to said raised portion.

17. A device as set forth in claim 1 wherein said sleeve carries means for facilitating securing it in position.

18. A device as set forth in claim 17 wherein said securing means comprise plastic material threads on said sleeve.

19. A device as set forth in claim 17 wherein said securing means comprise a portion of fabric of plastic material threads on said sleeve.

20. A device as set forth in claim 17 wherein said securing means are embedded into the wall of said sleeve at least on one side of said opening therethrough.

21. A device as set forth in claim 17 wherein said sleeve is of a rectangular cross-section providing narrow sides, and wherein said securing means are embedded in the wall of the sleeve at said narrow sides.

22. A device such as an implantable device for selectively opening and at least partially closing tubular organs of the body, comprising a sleeve of elastomeric plastic material adapted to embrace the organ, wherein the sleeve is relatively stiff and has a slit-like through opening for the organ, the width of the opening being such that the organ is at least partially closed off, and including at least at one narrow side of said through opening in the sleeve, a space which is closed with respect to the exterior, and at least one member which is disposed in said space and which is displaceable from the exterior, thereby to secure the device with its opening in a selected condition.

23. A device as set forth in claim 22 wherein said member in said space is a ball.

24. A device as set forth in claim 22 wherein said space, in a direction towards said opening, has a seat means for retainingly accommodating said displaceable member thereby to secure the device with said opening in a continuously open position.

25. A device as set forth in claim 24 wherein said space extends substantially in the plane of said opening and transversely with respect to the direction of flow in said organ to which said device is fitted.

26. A device as set forth in claim 24 wherein said space extends substantially in the plane of said opening and parallel with respect to the direction of flow in said organ to which said device is fitted.

27. A device as set forth in claim 26 wherein said space has first and second ends, wherein a respective seating means is provided at each of said ends, and wherein said space accommodates balls capable of being retainingly accommodated in respective ones of said seating means.

28. A device as set forth in claim 22 wherein a lubricant is contained in said space.

29. A device such as an implantable device for selectively opening and at least partially closing tubular organs of the body, comprising a sleeve of elastomeric plastic material adapted to embrace the organ, wherein the sleeve is relatively stiff and has a slit-like through opening for the organ, the width of the opening being such that the organ is at least partially closed off; wherein a space is provided at least in one wall of said through opening in the sleeve, said space being closed off with respect to said opening by a thin skin portion; and wherein a member is displaceable in said space, thereby to vary the width of said through opening.

30. A device as set forth in claim 29 wherein said member displaceable in said space is a pin.

31. A device as set forth in claim 29 wherein said member dispalceable in said space is a ball.

32. A device as set forth in claim 29 wherein said space defines at least one detent means for retaining said member in a selected position.

33. A device as set forth in claim 22 and further including a remote operating means for displacement of said member.

34. A device as set forth in claim 33 wherein said remote operating means comprises a stiff plastic tube which is embedded in silicone rubber, and an actuating member which is slideably mounted in said plastic tube and connected to said member, said actuating member being adapted to be actuated from the exterior.

35. A device as set forth in claim 29 and further including remote operating means for displacement of said member.

36. A device as set forth in claim 35 wherein said remote operating means comprises a stiff plastic tube which is embedded in silicone rubber, and an actuating member which is slidably mounted in said plastic tube and connected to said member, said actuating member being adapted to be actuated from the exterior.

37. A device as set forth in claim 22 wherein said displaceable member comprises polytetrafluoroethylene.

38. A device as set forth in claim 29 wherein said displaceable member comprises polytetrafluoroethylene.

39. A device as set forth in claim 1 wherein said sleeve includes a closed pressure chamber at least at a narrow side of said through opening in the sleeve, and further including a pump means communicating with said pressure chamber, and a pressure fluid filling said pressure chamber and said pump means.

40. A device as set forth in claim 39 and further including a conduit means connecting said pressure chamber to said pump means.

41. A device as set forth in claim 1 wherein said sleeve comprises silicone rubber.

* * * * *

UNITED STATES PATENT AND TRADEMARK OFFICE
CERTIFICATE OF CORRECTION

PATENT NO. : 4,643,169

DATED : February 17, 1987

INVENTOR(S) : Walter Koss et al

Page 1 of 5

It is certified that error appears in the above-identified patent and that said Letters Patent is hereby corrected as shown below:

In the Abstract, line 1, delete "Described is an" and insert --An--;

line 3, delete ". The device comprises" and insert --includes--.

Column 1, line 38, delete "expenditure" and insert --expense--;

line 39, delete "expenditure" and insert --expense--;

line 50, delete "closure" and insert --closed--;

line 55, delete "a success" and insert --successful--;

line 62, delete "and" (second occurrence);

UNITED STATES PATENT AND TRADEMARK OFFICE
CERTIFICATE OF CORRECTION

PATENT NO. : 4,643,169

DATED : February 17, 1987

INVENTOR(S) : Walter Koss et al

It is certified that error appears in the above-identified patent and that said Letters Patent is hereby corrected as shown below:

Column 1, line 63, after "without" insert --imposing--;

line 65, delete "occurring".

Column 2, line 19, delete "Those" and insert --These--;

line 43, delete "oesophagus" and insert --esophagus--.

Column 4, line 66, delete "that";

line 68, after "threads" insert --that--.

Column 5, line 5, delete "at" and insert --in--;

line 55, delete "then";

line 60, delete "then".

Column 6, line 22, delete "provided" and insert --,--;

UNITED STATES PATENT AND TRADEMARK OFFICE
CERTIFICATE OF CORRECTION

PATENT NO. : 4,643,169    Page 3 of 5
DATED     : February 17, 1987
INVENTOR(S) : Walter Koss et al It is certified that error appears in the above-identified patent and that said Letters Patent is hereby corrected as shown below:

line 23, after "passes" insert --, there--; same line, before "a" insert --provided--;

line 28, delete "When" and insert --As--;

lines 31-32, delete "the arrangement provides that as the member is displaced,";

lines 36-37, delete "thin skin portion" and insert --'thin skin portion'--;

line 37, delete "in respect of" and insert --with respect to--.

Column 7, line 34, delete "using";

line 47, after "ball," insert --respectively,--;

Column 7, line 63, delete "18" and insert --17--.

Column 8, line 22, after "tabs" insert --6--;

UNITED STATES PATENT AND TRADEMARK OFFICE
CERTIFICATE OF CORRECTION

PATENT NO. : 4,643,169

DATED : February 17, 1987

INVENTOR(S) : Walter Koss et al

It is certified that error appears in the above-identified patent and that said Letters Patent is hereby corrected as shown below:

Column 8, line 27, after "tabs" insert --6--;

line 30, after "opening" insert --5--;

line 31, after "opening" insert --5--;

line 40, after "opening" insert --5--;

line 54, delete "10" and insert --9--.

Column 9, line 5, after "opening" insert --5--;

line 23, after "opening" insert --5--.

Column 10, line 5, after "ball" insert --15--;

line 53, delete "and" and insert --through--;

line 54, delete "are" and insert --is--;

Column 10, line 64, after "seat" insert --17--.

Column 11, line 40, delete "of" and insert --, thus--.

UNITED STATES PATENT AND TRADEMARK OFFICE
CERTIFICATE OF CORRECTION

PATENT NO. : 4,643,169

DATED : February 17, 1987

INVENTOR(S) : Walter Koss et al

It is certified that error appears in the above-identified patent and that said Letters Patent is hereby corrected as shown below:

Column 12, line 14, delete "magnetisation" and insert --magnetic strength--.

Signed and Sealed this

Third Day of November, 1987

Attest:

DONALD J. QUIGG

Attesting Officer

Commissioner of Patents and Trademarks